United States Patent [19]
Brinkerhoff et al.

[11] Patent Number: 5,104,382
[45] Date of Patent: Apr. 14, 1992

[54] TROCAR

[75] Inventors: Ronald J. Brinkerhoff, Amelia; Earl J. Mills; Harry C. Parkhurst, both of Cincinnati, all of Ohio; Bela Vincze, Flemington, N.J.

[73] Assignee: Ethicon, Inc., Somerville, N.J.

[21] Appl. No.: 641,240

[22] Filed: Jan. 15, 1991

[51] Int. Cl.⁵ .......................... A61M 5/32; A61M 5/00
[52] U.S. Cl. ...................................... 604/165; 604/274
[58] Field of Search ............... 604/117, 170, 274, 273, 604/158, 272; 606/185

[56] References Cited

U.S. PATENT DOCUMENTS

| | | | |
|---|---|---|---|
| 2,623,521 | 12/1952 | Shaw | 604/170 |
| 3,817,251 | 6/1974 | Hasson | 128/348 |
| 4,168,699 | 9/1979 | Hauser | 128/768 |
| 4,177,814 | 12/1979 | Knepshield | 128/348 |
| 4,356,826 | 11/1982 | Kubota | 604/117 |
| 4,535,773 | 8/1985 | Yoon | 604/51 |
| 4,601,710 | 7/1986 | Moll | 604/165 |
| 4,650,030 | 3/1987 | Moll et al. | 604/165 |
| 4,653,475 | 3/1987 | Seike et al. | 604/165 |
| 4,850,973 | 7/1989 | Jordan et al. | 604/117 |
| 4,869,717 | 9/1989 | Adair | 604/274 |
| 4,902,280 | 2/1990 | Lander | 604/165 |
| 4,919,653 | 4/1990 | Martinez et al. | 604/117 |
| 4,931,042 | 6/1990 | Holmes et al. | 604/164 |
| 4,940,458 | 7/1990 | Cohn | 604/117 |

Primary Examiner—Paul J. Hirsch
Attorney, Agent, or Firm—Paul A. Coletti

[57] ABSTRACT

A safety trocar is provided which includes a spring-loaded shield that shields the cutting tip of the obturator after the obturator penetrates tissue. The distal end of the shield is hemispheric in profile and contains slides within cutting tip. The rounded distal end enables the shield to spring forward to shield the cutting tip as soon as the tip perforates the tissue. In other embodiments, positive mechanical means effect shielding.

26 Claims, 5 Drawing Sheets

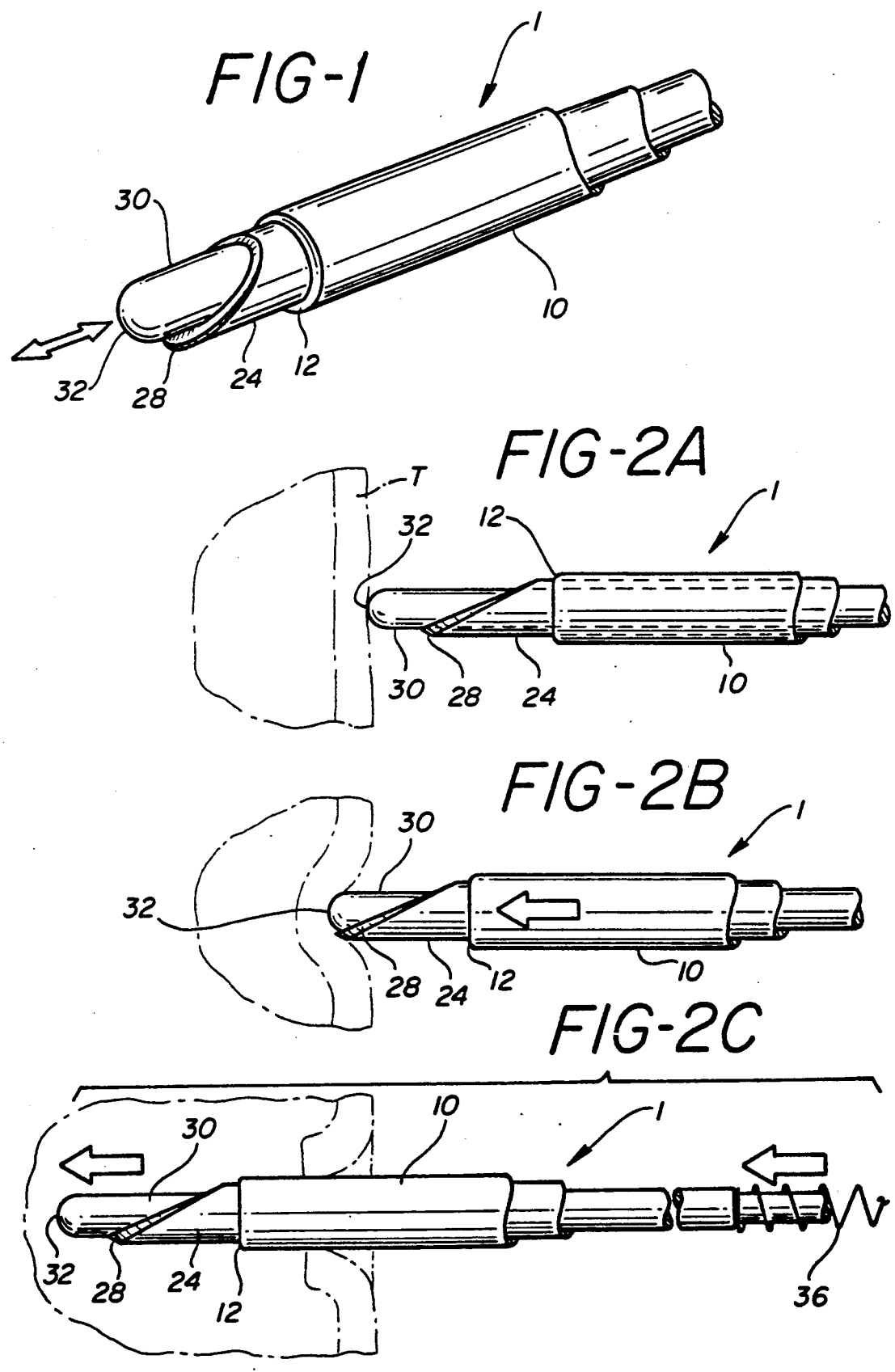

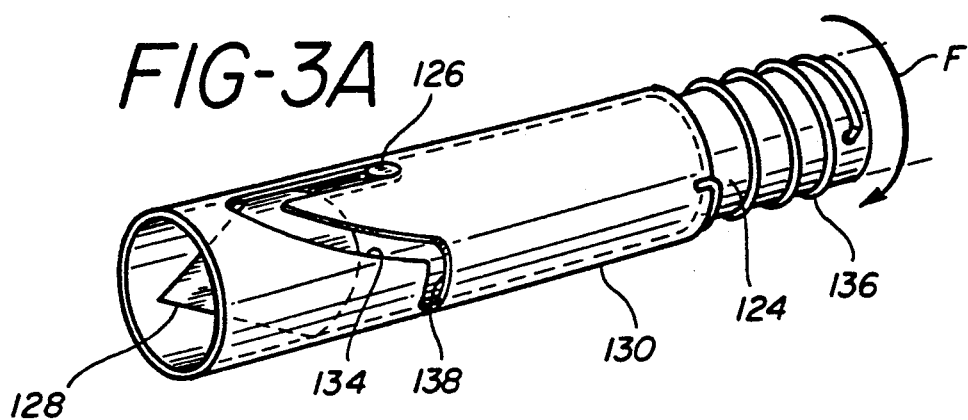
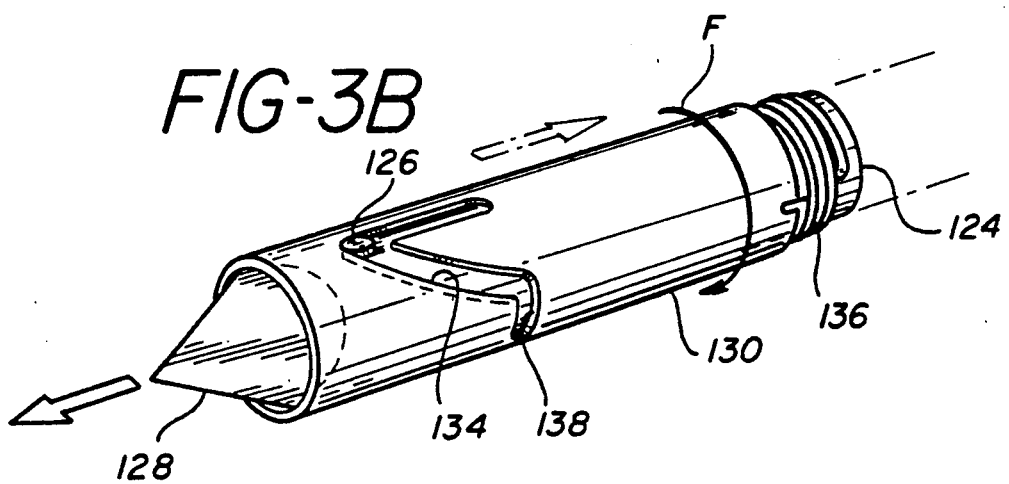
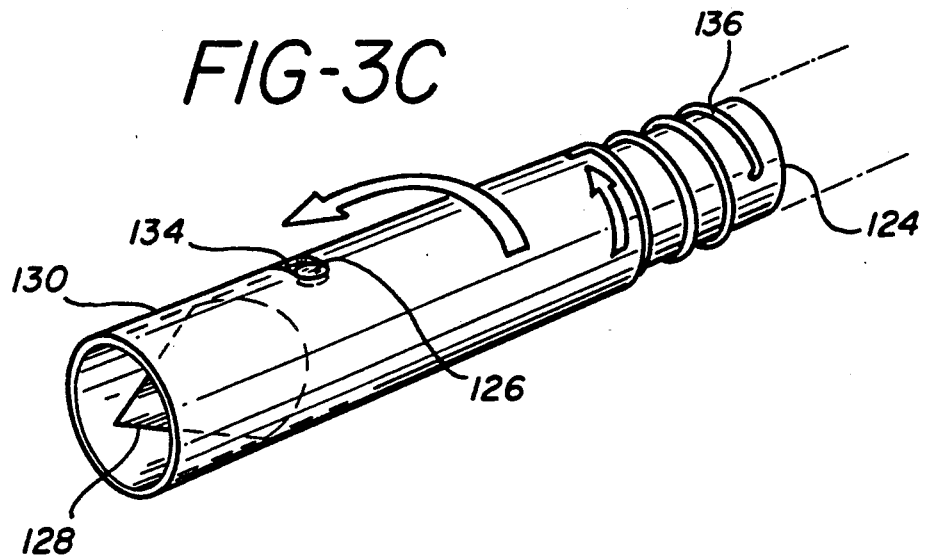

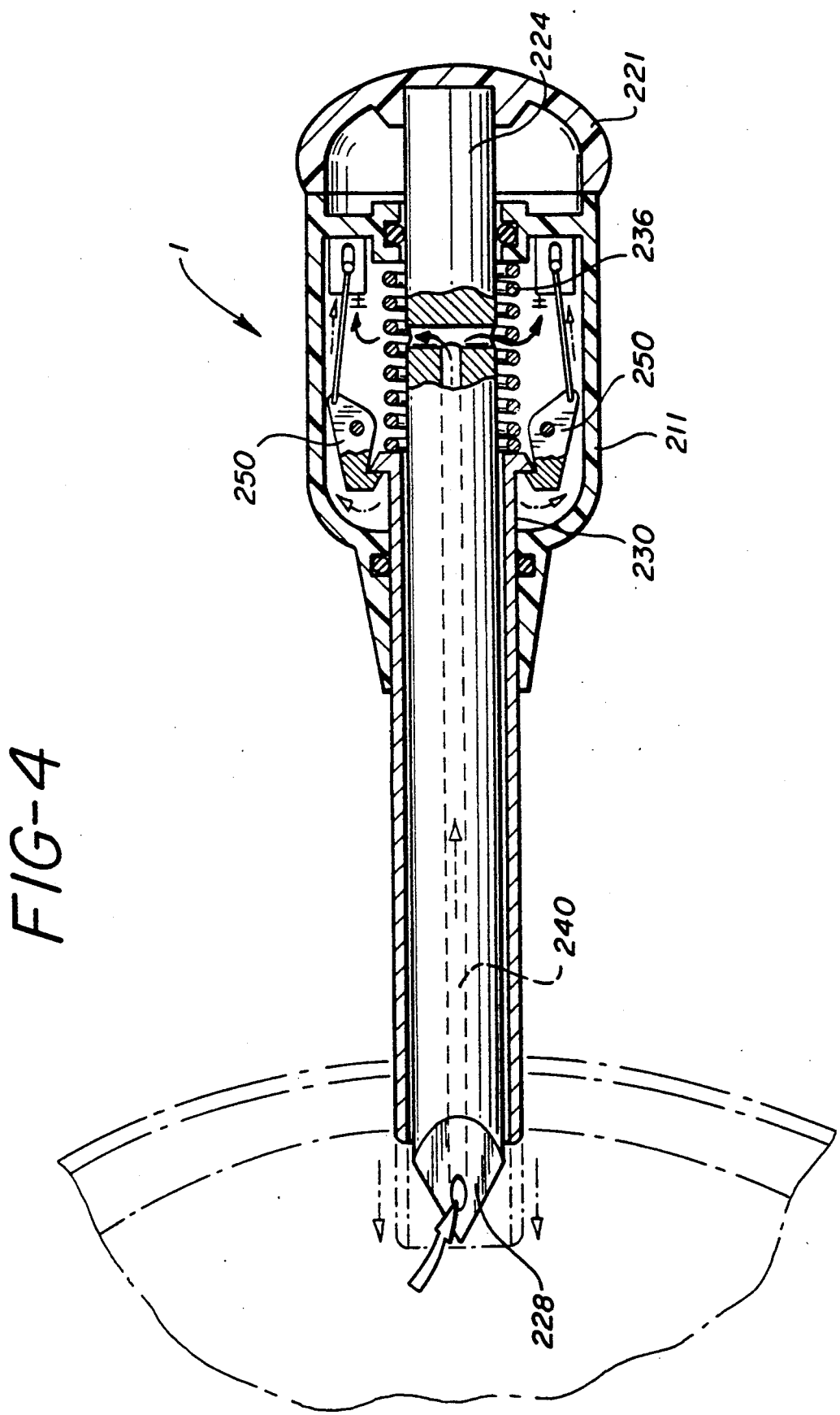

TROCAR

FIELD OF THE INVENTION

This invention relates to trocars used to puncture tissue for the performance of laparoscopic or arthroscopic surgery and, in particular, to such trocars which employ a safety device to shield the obturator point immediately after the point has perforated tissue.

BACKGROUND OF THE INVENTION

A trocar device generally comprises two major components, a cannula or tube and an obturator. The cannula contained in the trocar device is inserted through the skin to access a body cavity in which laparoscopic or arthroscopic surgery is to be performed. In order to penetrate the skin, the distal end of the trocar device is placed against the skin. The obturator has been inserted through the cannula. By pressing against the proximal end of the device, the point of the obturator is forced through the skin until it enters the body cavity. At this time the cannula is inserted through the perforation made by the obturator. Then, the obturator is withdrawn, from the cannula. The cannula is now an accessway to the body cavity.

It has been found that a great deal of force often is required to cause the obturator point to penetrate the skin and underlying tissue. When the point finally breaks through this tissue, resistance to penetration is suddenly removed, and the obturator point can suddenly penetrate to reach internal organs of the body, which may cause lacerations and other injury to the internal organs. To avert this danger to the patient, trocars have been developed which carry a spring-loaded tubular shield within the trocar tube and surrounding the obturator. The distal end of the shield will press against the skin as the obturator point penetrates the body until the obturator has formed a perforation with a diameter sufficient to allow the shield to pass through. At that time the resistance of the pierced tissue to the spring-loaded shield is removed, and the shield will spring forward to extend into the body cavity, surrounding the point of the obturator. The shield thus protects the internal body organs from inadvertent contact with the point of the obturator. A trocar including such a safety shield is described in Yoon, U.S. Pat. No. 4,535,773, for example.

The tubular shield in such a device will, however, require the incision formed by the obturator to extend to a considerable diameter before the resistance of the tissue pressure has been sufficiently decreased to allow the safety shield to spring forward. It is only when the obturator incision attains the diameter of the shield that the shield is fully able to spring into the body cavity. When the obturator employs a long, tapered cutting tip, this tip must extend a significant distance into the body before the incision is sufficiently enlarged to release the safety shield. It would therefore be desirable to provide a safety shield which will spring forward to shield the obturator tip as soon as possible after entry is gained to the body cavity.

Further patient safety would be provided by preventing the sudden extension of the obturator into the body cavity as the obturator tip fully penetrates the tissue. In some trocars means are provided which permit only incremental advancement of the obturator as tissue penetration proceeds. Such incremental advancement is provided by a ratchet or screw mechanism, for instance.

It would further be desirable to provide the trocar device with a safety shield, but in a device which reduces the component complexity of the trocar and tube with the spring-loaded safety shield. In accordance with still other trocars, the trocar tube is spring-loaded and employed as the safety shield. Thus, as the obturator point breaks through the tissue, the trocar tube will spring forward automatically into the body cavity, thereby providing shielding about the tip of the obturator.

SUMMARY OF THE INVENTION

In accordance with the principles of the present invention, there is disclosed a trocar which has a cannula with a generally hollow circular cross-section. Within this cannula is insertable an obturator having a sharpened tip and also containing a generally hollow circular cross-section. The obturator is insertable into the cannula and contains within the circular cross-section a shield. The shield has a blunt tip and is movable with respect to the obturator. The shield is urged away from the tip of the obturator by a compressible spring connected to the shield and the obturator and located within the handle portion of the obturator and away from the patient side of the trocar.

In accordance with further principles of the present invention, there is disclosed a trocar in which the obturator tip is shielded by a shield which surrounds the obturator tip. The tip is urged outside of the shield by spring means connected to the shield. There are positive placement means for maintaining the shield in a constantly urged forward position which comprise a channel placed in the shield placed within a mating relationship with a pin on the obturator. When it is desired to place the shield in a shielding position, the obturator tip is caused to rotate so that the shield with the pin inserted into the channel is not capable of moving relative to the channel. In this event, the obturator is closed over the tip.

Further, in accordance with the principles of the current invention, there are disclosed means to expose the obturator tip through the protective shield means which comprise control means. These control means are connected to the handle and cannula and are actuated such that the obturator tip is exposed from the shield by motion relative to the shield. This motion by the spring means attached to the handle causes the shield to move such that the shield and obturator are placed in position to expose the obturator tip. The control means may comprise manually operable means connected to the obturator, such as "ballpoint" or "pushbutton" means. Further, the control means can comprise piezoelectric sensor means capable of sensing pressure on the obturator such that the spring means is caused to be activated when pressure is above a certain known amount. In addition, there are latch means which are actuated by the sensor in order to cause the obturator to be exposed or shielded.

DETAILED DESCRIPTION OF THE DRAWINGS

These and other objects of the invention are more readily understandable from the attached drawings and detailed description in which, in the drawings:

FIG. 1 is a perspective view of trocar containing a shield, cannula and obturator tip with the shield placed in a protective position;

FIGS. 2a, 2b and 2c show the trocar of FIG. 1 such that the obturator is placed from a shielding to non-shielding position and then, after piercing through tissue, is again in a shielding position;

Figure 5:
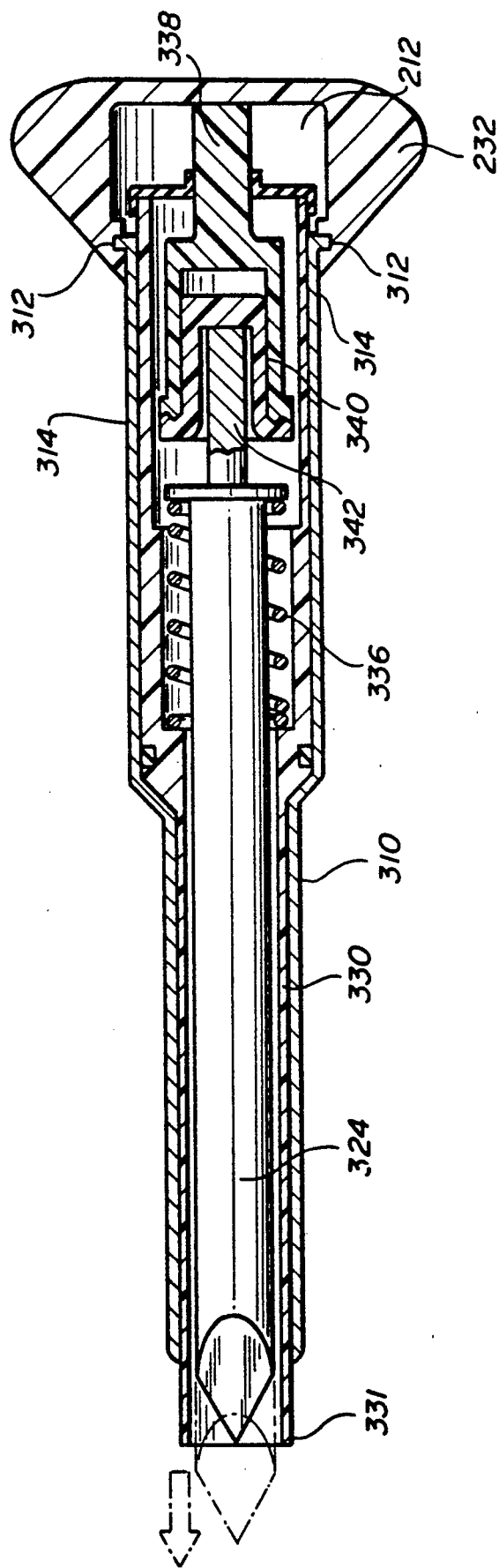
Figure 6:
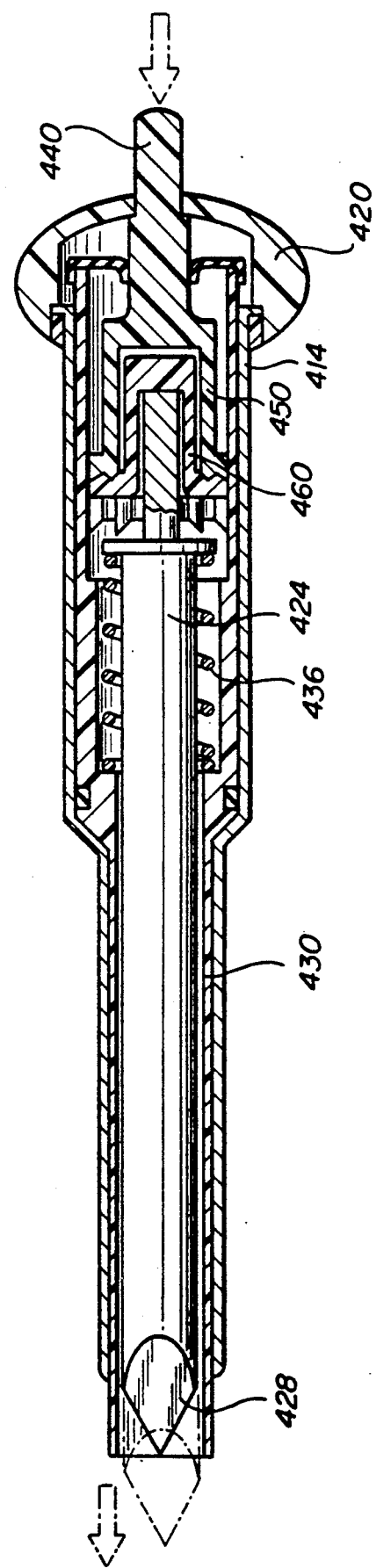

FIGS. 3a, 3b, and 3c disclose a shielding mechanism containing a pin and channel and shown in the shielding, non-shielding and preventive positions;

FIG. 4 is a cross-sectional view of a latching sensor mechanism which causes shielding of obturator tip;

FIG. 5 is a cross-sectional view of a manually operable obturator retracting mechanism with the shield in place; and FIG. 6 is a cross-sectional view of an alternative version of FIG. 5.

DETAILED DESCRIPTION OF THE INVENTION

A trocar 1 constructed in accordance with the principles of the present invention is shown in FIG. 1. The trocar includes a trocar tube or cannula 10 having an open distal end 12 and an open, flanged proximal end. The proximal end is mounted on a trocar handle not shown. There is an aperture in the proximal end of the handle which surrounds the cannula 10 and through which the cannula is mounted. This embodiment is more particularly described in Ser. No. 371,953 filed June 27, 1989 and entitled "Improved Safety Trocar", incorporated herein by reference. An obturator 24 is slideably and removably located inside the trocar cannula 10 and is inserted into the handle and trocar cannula by way of the open proximal end. At the proximal end of the obturator 24 is an obturator handle, and the distal end of the obturator 24 is sharpened to a point 28.

The trocar 1 of FIG. 1 is used to puncture a hole in soft tissue. The distal end 12 of the cannula 10 through the tissue. As better seen in FIG. 1, the obturator point 28 is hollow and contains within it a spring-loaded shield 30. This shield 30 is blunt-ended 32, and is forced by spring 36 seen in FIG. 2c so that the blunt-end 32 exceeds the tip 28 of the obturator 24. Thus, as seen in FIGS. 2a, 2b and 2c, when pressure is applied on the trocar, first, the tissue T will be contacted by the shield 30. Because the pressure of the tissue T is initially greater than the pressure of the spring 36 on the shield 30, the shield will be forced to retract into the trocar 1. This is seen more accurately in FIG. 2b.

Once the obturator tip 28 contacts the tissue T, as seen in FIG. 2b, the obturator tip 28 is able to pierce the tissue T. FIG. 2c shows the tissue T having been pierced by the obturator tip 28. The obturator tip 28 pierces through the tissue T and the blunt-ended shield 30 is forced forward to protect tissue from the obturator 24 by the spring-loaded end 32, as seen in FIG. 2c. Thus, the spring-loaded shield 30 protects internal organs while the trocar 1 is placed in the body cavity. Once the user has placed the cannula 10 in a position where it is desirable to be used, the obturator 24 with the shield 30 inside it is retracted entirely through the cannula 10 so that only the cannula 10 remains within the body cavity.

A separate embodiment of the invention is shown in FIGS. 3a, 3b and 3c. As seen in FIG. 3a, in this embodiment, the spring-loaded shield 130 is placed on the outside of the obturator 124. This spring-loaded shield 130 contains a channel or groove 134, as seen in FIG. 3a. Groove 134 interacts with a pin 126 on the obturator.

When pin 126 is placed in the generally longitudinal part of groove 134, spring 136 is in a loaded position, such that a force F is stored within spring 136. Thus, when the obturator 124 is forced against body tissue, as seen in FIG. 3b, the pin 124 travels along the channel 134 so that the obturator tip 128 is exposed. Force F continues to be stored in spring 136. When the user pierces the tissue, the action of the obturator causes spring 136 on the shield 130 to be rotated, as the force F acts on shield 130. This is seen in FIG. 3c. This rotation causes the obturator 124 to retract within the shield 130 and move into a closed position. Spring 136 is now in its relaxed state, and the "ledge" or latch 138 onto which the pin 126 sits, causes channel 134 to prevent movement of the shield 130 with respect to the obturator 124. At this point, the shield 130 is in a "locked" or shielding position. The obturator 124 is covered. Both shield and obturator can be moved and retracted through the cannula such as cannula 10 in FIGS. 1, 2a, 2b and 2c, so that a surgical procedure using the cannula 10 in the body cavity is possible.

Yet another alternate embodiment of this invention is seen in FIG. 4. Here, there is disclosed electric sensor means 240 which operates a latch means 250. This latch means 250 holds shield 230 which is acted on by a spring 236 within the obturator handle 232. Sensor means 240 causes the sliding latch 250 to hold the shield 230 in a non-shielding position so that the obturator 224 can pierce the body tissue. Upon sensing a marked change in pressure after penetration, the latch 250 is unlatched, and the shield 230 moves into a shielding position around obturator 224. The spring 236 forces shield 230 against the body cavity and after the obturator 224 has pierced the cavity, the spring 236 causes the shield 230 to protect the obturator tip 228. Again, both shield 230 and obturator 224 are removed through a cannula not shown, so that a procedure through the cannula is possible. Alternately, as shown in FIG. 4, the obturator 224, along with obturator handle 221 may be removed so that shield 230 acts as a cannula. Cannula handle remains in the body, and the procedure is possible through shield 230.

Yet another alternate embodiment of this invention is seen in FIG. 5. Here, the obturator 324 is exposed by a manually operated pressure means. As seen in FIG. 5, there is a hollow area 212 created in the rear of the obturator handle 232. This hollow portion abuts a projection 338. Projection 338 is connected by a series of concentric pieces 340, 342 to obturator 324. All these pieces 338, 340, 342 and obturator 324 slide within shield 330. Projection 338 slides relative to cannula 310 so that it causes obturator 324 locked inside shield 330 to be exposed at the end 331 of shield 330. This projection 338 causes the spring 336 to be compressed and this, in turn, forces obturator 324 to be exposed from shield 330, when a minimum pressure is created against the shield 330 and obturator 324. Once the pressure is overcome, that is once the tissue has been pierced, and force is removed from obturator handle 232 the spring 336 causes the obturator 324 to be retracted into the shield 330 so that the obturator 324 is shielded and the shield 330 is locked in place about the obturator 324. Of course, once the shield 330 is in place, the obturator 324 and shield 330 can be separated at connectors 312 from cannula handle 314 removed through the cannula 310 and a procedure can take place.

Finally, an alternate embodiment of the invention as seen in FIG. 5 is seen in FIG. 6. Here, pressure is supplied by the ball-point type mechanism as shown in FIG. 6. When the ball-point tip 440 is pressed, this causes the sliding mechanisms 450, 460 to move against the obturator 424 and further against the spring 436 holding the obturator 424. Thus, the obturator tip 428 may be exposed, as shown in phantom in FIG. 6. When it is so desired, the ball-point button 440 is again pressed and the shield 430 tip is caused to be unlatched. The mechanisms 450,460 act like a common ball-point pen mechanism with spring 436 to retract obturator 424. Thus, in this configuration the obturator tip 428 is again shielded by the now functional shield 430. Thus, the obturator 424 can be removed by obturator handle 420 through the cannula 410 from cannula handle 414 and a procedure can continue.

What has therefore been disclosed in all these embodiments is alternate configurations of a way to positively protect the obturator tip with a spring-biased shield. While the shield of this invention functions in ways similar to previous shields, none of the tips or shields previously disclosed are operable so that the shield is manually or electrically capable of moving into a more functional shielding position. In this way, the current invention is entirely different from previously disclosed inventions. Accordingly, it is to be understood that the present invention is to be derived from the appending claims, and their equivalents.

What is claimed is:

1. A surgical trocar comprising:
   a cannula handle, and a hollow cannula connected to said cannula handle;
   an obturator handle comprising an obturator with a sharpened tip connected to said obturator handle, a shield with a proximal end connected to said obturator handle and a distal end, and spring means connecting said obturator to said obturator handle such that said obturator is slidable relative to said shield; and
   control means attached to said obturator handle and interoperative with said spring means to generally urge said obturator tip past said shield distal end.

2. The trocar of claim 1 wherein said control means comprises slide means located within said obturator handle, said slide means movable between an open position to expose said obturator tip, and a closed position wherein said obturator tip is protected by said shield distal end.

3. The trocar of claim 2 wherein said control means further comprises push button means extending through said obturator handle, said push button cooperating with said slide means to place said obturator in either of said closed or open positions.

4. The trocar of claim 2 further comprising positive placement means comprising a channel on said shield placed in mating relationship with a pin on said obturator and wherein said channel contains a longitudinal portion for positively urging said pin away from said spring means, and a closure portion connected to said longitudinal portion operable by rotating said shield about said obturator such that said pin is guided within said closure portion to a position restricting longitudinal movement of said shield with said obturator.

5. The trocar of claim 4 wherein said closure portion contains a curved section and a lateral section, said pin movable from said longitudinal portion into said curved section by rotation of said shield such that motion is restricted longitudinally when said jaw is seated in said lateral section.

6. The trocar of claim 2 wherein said shield has a generally blunt end.

7. The trocar of claim 1 wherein said control means are further capable of causing said tip to retract from said open position to a closed position where said tip is enclosed by said shield.

8. The trocar of claim 7 wherein said shield is fixed within said cannula during motion of said obturator tip relative to said shield.

9. The trocar of claim 2 said control means further comprising sensor means attached to said shield and said obturator, said sensor means capable of sensing pressure on said obturator or said shield and activating said shield to said open position to expose said tip from said shield.

10. The trocar of claim 9 wherein said control means are further capable of causing said tip to retract from said open position to a closed position where said tip is enclosed by said shield.

11. The trocar of claim 9 further comprising latch means connected to said sensor and said shield and activated by said sensor to hold said shield in said open portion.

12. The trocar of claim 11 wherein said control means, said obturator and said shield are contained within a handle, said handle enabling insertion of said obturator and said shield into said cannula.

13. The trocar of claim 11 wherein said sensor is electro-mechanical and attached to said obturator tip to sense pressure on said tip.

14. A trocar comprising:
   an obturator having a sharpened tip;
   a shield capable of extending past said tip, said shield connected to said obturator and movable relative to said obturator;
   said tip connected by spring means to said shield; and
   positive placement means comprising a channel in said shield placed in mating relationship with a pin on said obturator wherein said channel contains a longitudinal portion for positively urging said pin away from said spring means, and a closure portion connected to said longitudinal portion operable by rotating said shield about said obturator such that said pin is guided within said closure portion to a position restricting longitudinal movement of said shield with said obturator.

15. The trocar of claim 14 wherein said closure portion contains a curved section and a lateral section, said pin movable from said longitudinal portion into said curved section by rotation of said shield and into said lateral section by further rotation of said shield such that motion is restricted longitudinally when said jaw is seated in said lateral section.

16. The trocar of claim 14 further comprising a cannula with a generally hollow circular cross-section, said obturator with generally hollow circular cross-section and insertable within said cannula, and said shield movable with respect to said obturator and insertable within said obturator hollow cross-section.

17. The trocar of claim 14 wherein said shield has a generally blunt end.

18. The trocar of claim 14 wherein said shield is urged to extend past the tip of said obturator by said spring means connected to said shield.

19. The trocar of claim 16 wherein said spring means and said obturator are connected to a handle, said handle holding said spring means in place to maintain said shield within said obturator and extend past said obturator tip.

20. The trocar of claim 19 wherein said shield is placed inside said obturator on said handle and is insertable into said cannula.

21. The trocar of claim 20 wherein said shield is capable of being held by latching means to expose said obturator tip from said cannula.

22. The trocar of claim 14 further comprising sensor means attached to said shield and said obturator, said sensor means capable of sensing pressure on said obturator or said shield and activating said shield to an open position to expose said tip from said shield.

23. The trocar of claim 22 wherein said sensor means are further capable of causing said tip to retract from said open position to a closed position where said tip is enclosed by said shield.

24. The trocar of claim 22 further comprising latch means connected to said sensor and said shield and activated by said sensor to hold said shield in said open portion.

25. The trocar of claim 24 wherein said control means, said obturator and said shield are contained within a handle, said handle enabling insertion of said obturator and said shield into said cannula.

26. The trocar of claim 24 wherein said sensor is electro-mechanical and attached to said obturator tip to sense pressure on said tip.

* * * * *